United States Patent
Thienpont et al.

(10) Patent No.: US 10,429,295 B2
(45) Date of Patent: Oct. 1, 2019

(54) METHOD AND APPARATUS FOR THE DETECTION OF THE PRESENCE OF MYCOTOXINS IN CEREALS

(71) Applicant: TOMRA SORTING N.V., Leuven (BE)

(72) Inventors: Hugo Thienpont, Gooik (BE); Wendy Meulebroeck, Deurne (BE); Lien Smeesters, Brasschaat (BE)

(73) Assignee: TOMRA SORTING N.V., Leuven (BE)

( * ) Notice: Subject to any disclaimer, the term of this patent is extended or adjusted under 35 U.S.C. 154(b) by 0 days.

(21) Appl. No.: 16/079,488

(22) PCT Filed: Feb. 23, 2017

(86) PCT No.: PCT/EP2017/054227
§ 371 (c)(1),
(2) Date: Aug. 23, 2018

(87) PCT Pub. No.: WO2017/144608
PCT Pub. Date: Aug. 31, 2017

(65) Prior Publication Data
US 2019/0056319 A1 Feb. 21, 2019

(30) Foreign Application Priority Data
Feb. 24, 2016 (EP) ..................... 16157206

(51) Int. Cl.
*G01N 21/17* (2006.01)
*G01N 21/3563* (2014.01)
*G01N 21/47* (2006.01)

(52) U.S. Cl.
CPC ..... *G01N 21/3563* (2013.01); *G01N 21/4738* (2013.01); *G01N 2201/065* (2013.01); *G01N 2201/129* (2013.01)

(58) Field of Classification Search
CPC .......... G01N 21/3563; G01N 21/4738; G01N 2201/065; G01N 2201/129
See application file for complete search history.

(56) References Cited

U.S. PATENT DOCUMENTS

| | | |
|---|---|---|
| 6,865,408 B1 | 3/2005 | Abbink et al. |
| 7,671,985 B1 | 3/2010 | Milosevic et al. |

FOREIGN PATENT DOCUMENTS

| | | |
|---|---|---|
| CN | 103575694 A | 2/2014 |
| WO | 2012095651 A1 | 7/2012 |

OTHER PUBLICATIONS

Dvoracek et al. "Near infrared spectroscopy for deoxynivalenol content estimation in intact wheat grain" Crop Research Institute, Prague-Ruzyne, Czech Republic, Plant Soil Environ.,58 2012 (4); p. 196-203 (Year: 2012).*

(Continued)

*Primary Examiner* — David P Porta
*Assistant Examiner* — Mamadou Faye
(74) *Attorney, Agent, or Firm* — Buchanan Ingersoll & Rooney P.C.

(57) ABSTRACT

A method and apparatus for detecting the presence of mycotoxins in cereals, the method including: capturing at least one diffuse-light absorption spectrum of a collection of cereal grains; capturing at least one diffuse-light absorption spectrum of at least one individual cereal grain from the collection of cereal grains; and classifying the level of mycotoxin contamination in at least one cereal grain by performing multivariate data analysis on the at least one diffuse-light absorption spectrum of the collection of cereal grains and the at least one diffuse-light absorption spectrum of the at least one individual cereal grain.

15 Claims, 7 Drawing Sheets

(56) References Cited

OTHER PUBLICATIONS

Pearson et al. "Reduction of Aflatoxin and Fumonisin Contamination in Yellow Corn High-Speed Dual-Wavelength Sorting", American Association of Cereal Chemists, Inc., 2004, p. 490-498 (Year: 2004).*
International Search Report (PCT/ISA/210) dated Mar. 22, 2017, by the European Patent Office as the International Searching Authority for International Application No. PCT/EP2017/054227.
Written Opinion (PCT/ISA/237) dated Mar. 22, 2017, by the European Patent Office as the International Searching Authority for International Application No. PCT/EP2017/054227.
Dowell, F. E., et al., "Predicting Scab, Vomitoxin, and Ergosterol in Single Wheat Kernels Using Near-Infrared Spectroscopy", Cereal Chemistry, vol. 76, No. 4, Jul. 1, 1999, pp. 573-576.
Dvořáček, V., et al., "Near infrared spectroscopy for deoxynivalenol content estimation in intact wheat grain", Plant Soil Environ., vol. 58, , pp. 196-203.

\* cited by examiner

METHOD AND APPARATUS FOR THE DETECTION OF THE PRESENCE OF MYCOTOXINS IN CEREALS

TECHNICAL FIELD

The present invention relates to cereal contamination. In particular, the present invention provides a method and apparatus for the detection of the presence of mycotoxins in cereals.

BACKGROUND ART

The presence of mycotoxins, secondary metabolites of toxic fungi, in agricultural commodities is worldwide a major problem. According to the Food and Agricultural Organization (FAO) estimates, 25% of the world's food crops are affected by mycotoxin producing fungi (Rasch, Kumke, & Löhmannsröben, 2010). The most important mycotoxins in food and feed production, that pose a major threat to public health and agro-economy, include aflatoxins, deoxynivalenol (DON), ochratoxin A, fumonisin, zearalenone, patulin and T-2 toxin (Miller, 1995; Traar, 2013).

DON is among the most prevalent mycotoxins and is mostly produced by the moulds fusarium graminearum and fusarium culmorum. It frequently occurs on cereal commodities, like wheat, maize, barley, oats and rye, which can be infected before or after the harvest (Sobrova et al., 2010). Moreover, because DON cannot be destroyed during food processing, like cooking, freezing and roasting, it appears both in the raw and processed products. The ingestion of DON-contaminated products can cause acute and chronic health effects such as diarrhea, nausea, immunosuppression and neurotoxicity (Abysique, Tardivel, Troadec, & Felix, 2015; Pestka, 2007). The detection of DON is an important issue in the food industry, because it is present in more than 90% of all mycotoxin-contaminated cereal samples and its occurrence is considered to be an indicator of the presence of other mycotoxins. (Ran et al., 2013)

DON is an important contaminant of maize (Pleadin et al., 2012) and maize is the staple food in many countries. Currently, the presence of DON in food and feed products is strictly regulated in most regions of the world. Regarding raw maize kernels, the European Commission states the maximum allowed DON concentration to be 1750 ppb, while in the USA and China a limit of 1000 ppb of DON is imposed (European Commission, 2007). To fulfil these limits, the presence of DON is nowadays mostly detected by the use of chemical analyses, like liquid chromatography—tandem mass spectrometry (LC-MS/NIS) and enzyme-linked immunosorbent assays (ELISA). However, these analytical techniques are time-consuming, expensive and destructive (Ran et al., 2013). Due to the uneven presence of the toxin in both the food products and the crops, these sample-based analyses often give a limited view on the degree of contamination. It is an aim of the present invention to provide a non-destructive spectroscopic method that can be used to screen individual, cereal kernels and other food products suseptable to contamination with non-fluorescent mycotoxins.

Spectroscopic detection techniques are already widely used in agriculture and chemical industries for the determination of organic compounds in matter, like proteins, moisture, starch and pigments (Baye, Pearson, & Settles, 2006; K. C. Volkers, M. Wachendorf, R. Loges, N. J. Jovanovic, 2003; Meulebroeck & Thienpont, 2012). To date, there is a high interest to apply the spectroscopic detection techniques for the identification of DON. The use of Fourier-transform near- and mid-infrared (FT-NIR and FT-MIR) spectroscopy for the detection of DON in wheat and maize is already widely discussed (Abramović, Jajić, Abramović, Ćosić, & Jurić, 2007; De Girolamo, Cervellieri, Visconti, & Pascale, 2014; Kos, Lohninger, & Krska, 2003). However, current published measurements use homogeneously contaminated, grinded samples and require the use of chemometrics to classify the samples into their various contamination levels. It is an aim of the present invention to provide a spectroscopic method that enables the measurement of the localized contamination in unground, individual cereal kernels, such as maize kernels. Furthermore, due to its vibration sensitivity, Fourier-transform spectroscopy can hardly be implemented in an industrial environment.

SUMMARY OF INVENTION

According to the present invention there is provided a method for detecting the presence of mycotoxins in cereals, the method comprising:
  capturing at least one diffuse-light absorption spectrum of a collection of cereal grains;
  capturing at least one diffuse-light absorption spectrum of at least one individual cereal grain from the collection of cereal grains;
  classifying the level of mycotoxin contamination in at least one cereal grain by performing multivariate data analysis on the at least one diffuse-light absorption spectrum of the collection of cereal grains and the at least one diffuse-light absorption spectrum of the at least one individual cereal grain.

Preferably, each diffuse-light absorption spectrum is captured using an integrating sphere. Preferably, the diffuse-light absorption spectrum of the individual cereal grain is captured using an integrating sphere which is smaller than that used to capture each diffuse-light absorption spectrum of the collection of cereal grains. Preferably, the or each diffuse-light absorption spectrum of the collection of cereal grains is captured by illuminating the collection in the centre of an integrating sphere. Preferably, the or each diffuse-light absorption spectrum of the individual cereal grain is captured by illuminating the cereal grain while in front of an aperture of a sample port of an integrating sphere.

Preferably, the step of capturing at least one diffuse-light absorption spectrum of an individual cereal grain comprises capturing multiple diffuse-light absorption spectra by illuminating multiple regions of the cereal grain.

In one embodiment, the step of classifying the level of mycotoxin contamination in at least one cereal grain comprises calculating the ratio between the reflectance at a first selected wavelength and the reflectance at a second selected wavelength; and classifying the level of mycotoxin contamination in at least one cereal grain based on the calculated ratio. Preferably, the selected wavelengths are in the wavelength region of 700 nm to 1500 nm. In alternative embodiments, the ratio may be calculated based on the reflectance at more than two selected wavelengths.

In a further embodiment the step of classifying the level of mycotoxin contamination in at least one cereal grain uses chemometric techniques. A chemometric method such as principle components analyses may be used to classify the level of mycotoxin contamination in an individual cereal grain. Chemometric methods are advanced techniques requiring a large arithmetric power of the machine in which they are used.

The method may further comprise calculating a mean diffuse-light absorption spectrum of a collection of cereal grains if multiple diffuse-light absorption spectra are captured and wherein the step of classifying the level of mycotoxin contamination in at least one cereal grain comprises performing multivariate data analysis on a mean spectrum.

The method may further comprise calculating a mean diffuse-light absorption spectrum of at least one cereal grain if multiple diffuse-light absorption spectra of the cereal grain are captured and wherein the step of classifying the level of mycotoxin contamination in at least one cereal grain comprises performing multivariate data analysis on a mean spectrum.

Each diffuse-light absorption spectrum captured may be a NIR diffuse-light absorption spectrum. Alternatively, each diffuse-light absorption spectrum captured may be a visible and NIR diffuse-light absorption spectrum.

Classifying the level of mycotoxin contamination in at least one cereal grain may comprise comparing at least one captured spectrum with a spectrum of an uncontaminated grain and identifying differences between the spectra. Classifying the level of mycotoxin contamination in at least one cereal grain may comprise comparing at least one captured spectrum with a more than one spectrum of at least one uncontaminated grain and identifying differences between the spectra. The method may further comprise obtaining the spectrum of an uncontaminated grain from a database of grain spectra. The method may further comprise identifying the cereal type of the collection of cereal grains by comparing at least one captured spectrum to a plurality of sample spectra in the database to find the best fit. Alternatively the method may further comprise identifying the cereal type from a user input.

The present invention further provides a computer readable medium containing program instructions which when executed by a processor cause the processor to perform the above method.

The present invention further provides an apparatus for detecting the presence of mycotoxins in cereals, comprising:
  means for capturing at least one diffuse-light absorption spectrum of a collection of cereal grains;
  means for capturing at least one diffuse-light absorption spectrum of at least one individual cereal grain from the collection of cereal grains; and
  means for classifying the level of mycotoxin contamination in at least one cereal grain by performing multivariate data analysis on the at least one diffuse-light absorption spectrum of the collection of cereal grains and the at least one diffuse-light absorption spectrum of the at least one individual cereal grain.

Preferably, each means for capturing a diffuse-light absorption spectrum comprises an integrating sphere. Preferably, the means for capturing at least one diffuse-light absorption spectrum of the individual cereal grain comprises an integrating sphere which is smaller than that used to capture each diffuse-light absorption spectrum of the collection of cereal grains.

Preferably, the apparatus further comprises means for capturing multiple diffuse-light absorption spectra by illuminating multiple regions of the cereal grain. The means for capturing at least one diffuse-light absorption spectrum may comprise means for capturing at least one NIR diffuse-light absorption spectrum. The means for capturing at least one diffuse-light absorption spectrum may comprise means for capturing at least one UV, visible and MR diffuse-light absorption spectrum.

The means for classifying the level of mycotoxin contamination in at least one cereal grain may comprise means for comparing at least one captured spectrum with a spectrum of an uncontaminated grain and means for identifying differences between the spectra.

The apparatus may further comprise means for obtaining the spectrum of an uncontaminated grain from a database of grain spectra.

The apparatus may further comprise means for identifying the cereal type of the collection of cereal grains by comparing at least one captured spectrum to a plurality of sample spectra in the database to find the best fit. The apparatus may further comprise means for identifying the cereal type from a user input.

The present invention is suitable for any type of cereal, including but not limited to wheat, maize, barley, oats and rye. In food products, mycotoxin is bound to several substances (like proteins). These bindings influence the reflection spectrum of the food product. onsequently, it is possible to indirectly observe mycotoxin contamination by measuring its influence onto the matrix of a food product. The higher the mycotoxin-contamination within a food product, the larger its influence onto the matrix and so also its influence on the reflection spectrum of the product.

When a light source illuminates a sample, the incident light rays will be absorbed, transmitted and reflected, depending on the chemical composition and the physical properties of the sample. To optically identify the mycotoxin contamination, the present invention utilises diffuse-light absorption spectroscopy to study the scatter-independent reflection properties of products. This may be achieved through the use of an integrating sphere which collects all reflected light, independent of the reflection angle.

By using an integrating sphere, all scattered and reflected light (so both direct (specular) as diffuse reflection) is collected. When a light beam illuminates the sample, light will be scattered, transmitted, reflected and absorbed. Only the light that is absorbed by the sample will not be collected by the detector. An integrating sphere allows the amount of the incoming light that is absorbed by the sample to be measured. It is therefore possible to detect a retransmitted light signal after interaction with the grain, the light having penetrated at the point of illumination (where direct and diffuse reflection would occur), been scattered and otherwise interacted with the product and then re-emitted from the grain in the proximity of but not at the illumination point.

In a first step, a large integrating sphere in which different cereal kernels can be positioned may be used, so that the optimum wavelength regions can be identified. Furthermore, when considering an unsorted, contaminated sample, this setup enables the rapid measurement of a large amount of cereal kernels, allowing a rough pre-classification of the samples. In the second step, the reflection spectra of individual cereal kernels with a smaller integrating sphere may be investigated, to classify the kernels according to their localized contamination level.

The present invention uses diffuse-light absorption spectroscopy as a non-destructive optical detection technique for the identification of mycotoxins such as DON in solid cereal kernels. The results of the present invention can enable the fast, accurate and non-destructive detection of mycotoxins such as DON that is suited for implementation in industrial in-line scanning machines. Because of the inhomogeneous mycotoxins-contamination, the ability to monitor the contamination of individual cereal kernels is indispensable to increase food safety and to reduce economical losses.

BRIEF DESCRIPTION OF THE DRAWINGS

Embodiments of the invention will be described, by way of example only, with reference to the accompanying drawings in which.

DESCRIPTION OF EMBODIMENTS

Figure 1:
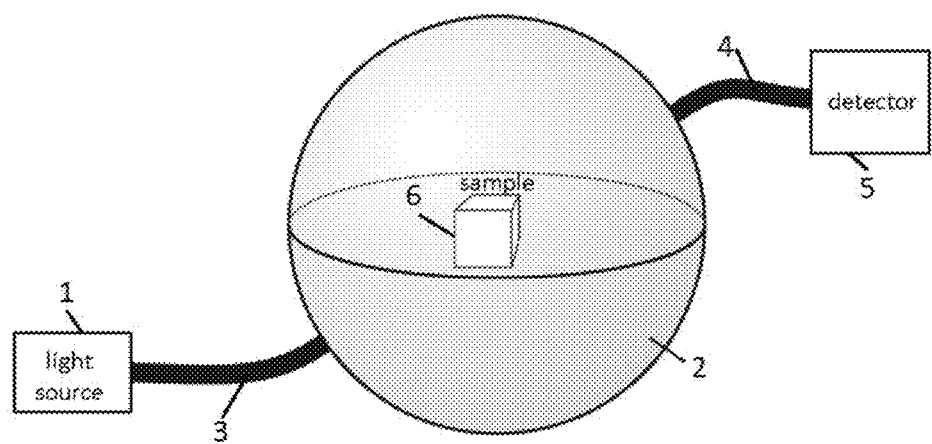
FIG. 1 shows a first part of an apparatus for the detection of mycotoxins in cereals, in accordance with one embodiment of the invention.

An apparatus for the detection of mycotoxins in cereals, in accordance with one embodiment of the invention, is shown in FIG. 1. The apparatus shown in FIG. 1 facilitates a two-stage measurement procedure. Both stages measure the diffuse-light absorption spectra, but use a different type of integrating sphere. The first stage uses a larger reflection integrating sphere, allowing a fast screening of a collection of cereal kernels, while the second stage uses a smaller reflection integrating sphere, enabling the measurement of individual kernels. For example the larger integrating sphere may have a diameter of 25 cm while the smaller integrating sphere may have a diameter of 6 cm. Other size combinations are of course possible.

The first-stage measurement setup is used to capture at least one diffuse-light absorption spectrum of a collection of cereal grains. The first stage in FIG. 1 consists of a supercontinuum light source 1, a larger reflection integrating sphere 2, optical fibres 3, 4 and a spectrum analyser 5. A collection of cereal kernels 6 can be positioned inside the sphere.

The kernels may be contained in a Petri dish or otherwise contained. The outside of the sphere 2 contains different ports, to which the illumination light source and the detecting fibre can be connected. A bright light source is preferable to reduce the measurement duration, while obtaining a large signal-to-noise ratio. Light source used to illuminate the sample-under-test may be a pigtailed supercontinuum source. The reflected light is captured by detection fibre 4. When no sample is present in the integrating sphere, the illumination light will be almost completely collected by the detection fibre, after its diffuse reflections onto the reflective coating inside the sphere.

When a sample is inserted in the sphere, the captured light will be influenced by its absorbance, and thus also by its specific composition. Considering the Petri dishes with cereal, almost the entire surface of the kernels is illuminated, resulting in the measurement of their mean contamination level since the reflectance spectra of both the low and high contaminated areas are captured. Subsequently, the detection fibre guides the captured light from the integrating sphere to the spectrum analyser, which measures the light intensity as function of the wavelength. The spectrum analyser may be a broadband spectrum analyser, consisting of two different channels with linear detector arrays, enabling the simultaneous measurement of both the visible and NIR spectrum. The first channel may be able to measure the spectrum between 200 nm and 1100 nm, with a resolution of 1.4 nm. The second channel may be able to measure the spectrum between 1000 nm and 1700 nm, with a resolution of 4 nm. The spectra may be visualized using software.

Prior to each measurement, a dark and reference spectrum may be captured. The reference spectrum represents the light source spectrum and may be obtained while measuring an empty Petri dish. The dark spectrum visualises the background light and was obtained when capturing the spectrum without illumination source. The reflection spectrum of each cereal Petri dish may be captured multiple times, after which the mean spectrum may be calculated.

Based on the reflected light intensity of the cereal kernels ($I_{cereal}$) the intensity of the dark spectrum ($I_{dark}$) and the intensity of the reference spectrum ($I_{reference}$), the reflectance, for every wavelength ($\lambda$), may be calculated by using the following formula:

$$\text{Reflectance } (\lambda) = (I_{cereal}(\lambda) - I_{dark}(\lambda))/(I_{reference}(\lambda) - I_{dark}(\lambda)) \quad (1)$$

Because this first-stage setup allows the measurement of the cumulative contamination, the reflection differences between low and high contaminated cereal samples are increased, resulting in an accurate determination of the spectral contrast.

Figure 2:
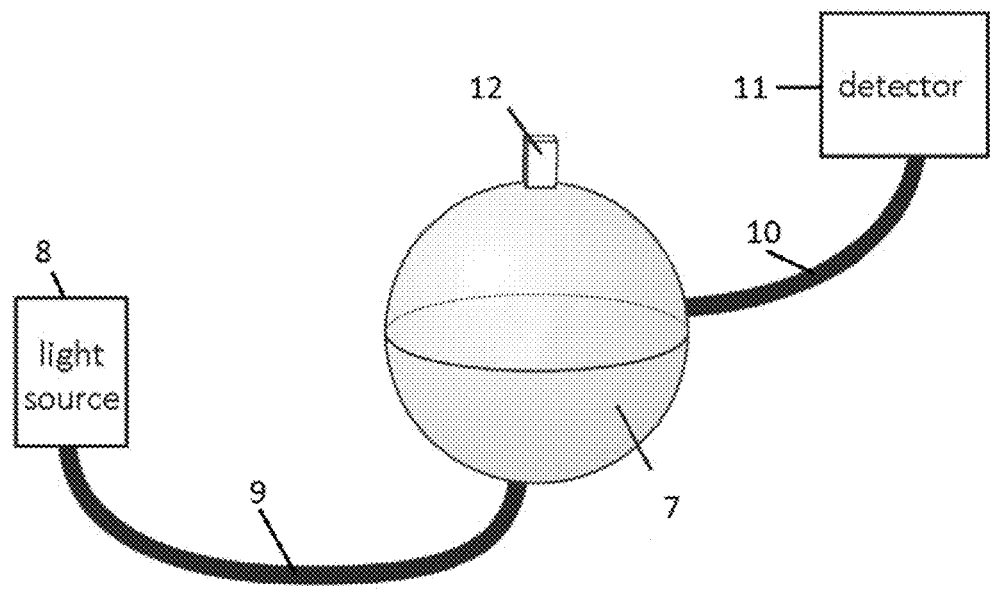
FIG. 2 shows a second part of an apparatus for the detection of mycotoxins in cereals, in accordance with one embodiment of the invention.

The second-stage measurement setup is used to measure the reflectance of individual cereal kernels by using a compact integrating sphere. FIG. 2 shows the second-stage measurement setup in accordance with one embodiment of the invention, which allows the investigation of individual cereal kernels, using a compact integrating sphere 7. The apparatus comprises a spectral broadband light source 8, optical fibres 9, 10, a collimating lens, a small reflection integrating sphere 7 and a spectrum analyser 11. However, the sample 12 can now not be positioned inside the sphere, but needs to be positioned in front of the aperture of the sample port. This aperture limits the illuminated area of the cereal kernel surface and enables the investigation of its localized contamination. The exterior of the integrating sphere contains two connectors, at which the illumination and detection fibre can be connected. Since the integrating sphere is smaller than that used in the first stage setup, the illumination power can be decreased, allowing the use of a deuterium and halogen light bulb instead of the high power supercontinuum source. The combination of a deuterium and halogen pigtailed source, emitting light from 200 nm to 2500 nm, shows a more stable spectrum than the supercontinuum source and enables the study of the UV spectral region. The light at the end of deuterium and halogen pigtailed source fibre is coupled into the illumination fibre, which is connected to the integrating sphere. To minimize the light loss during this coupling, a collimating lens is attached to the illumination fibre, transmitting light from 200 nm to 2500 nm. After the illumination of the sample, all reflected light is captured by the integrating sphere, allowing a quantitative analysis. Subsequently, the reflected light is collected by the detection fibre, which guides this light to the spectrum analyser. The same two-channel spectrum analyser as in the first-stage configuration is used, measuring the spectrum from 200 nm until 1700 nm.

The reflectance is calculated using equation (1). Prior to the measurement of the cereal kernels, the reference and dark spectrum may be determined. The reference spectrum, corresponding with the source spectrum, may be measured when positioning a 99.9% reflective tile at the aperture of the integrating sphere. The dark spectrum measures the light intensity captured by the detection fibre without a sample on top of the integrating sphere. After the dark and reference measurements, the reflection spectra of the individual cereal kernels may be captured. Each cereal kernel may be illuminated at multiple positions. To avoid background light entering the aperture of the sphere, all measurements may be performed in a dark environment.

Figure 3:
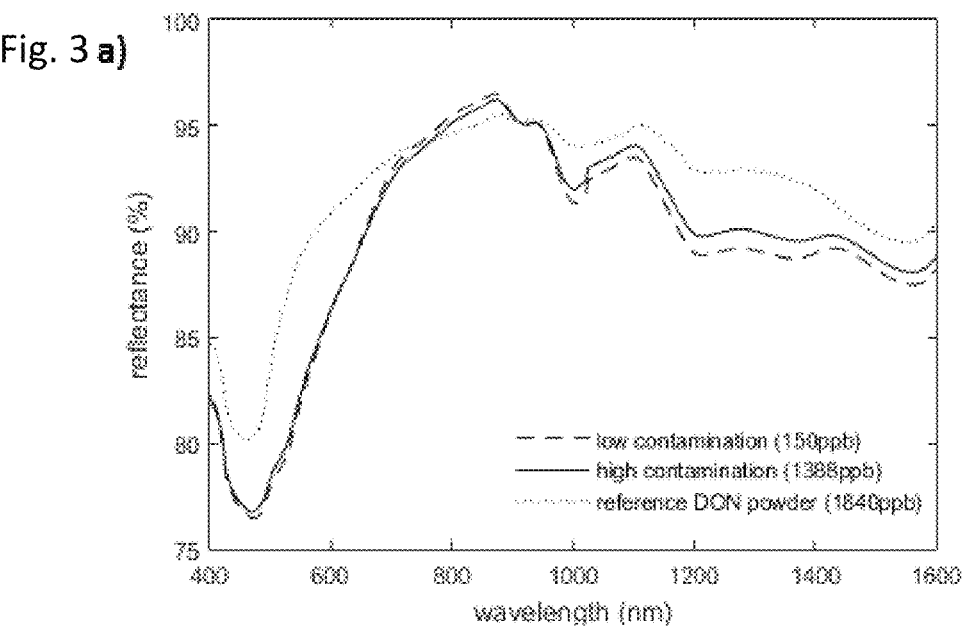
FIGS. 3(a) and 3(b) show the mean reflection spectra of test maize kernels and a reference DON-contaminated maize powder, measured with a 250 mm-reflection integrating sphere: (a) vis-NIR spectrum; (b) NIR wavelength range showing the largest spectral contrast between the low and high contaminated maize kernels.
Figure 3:
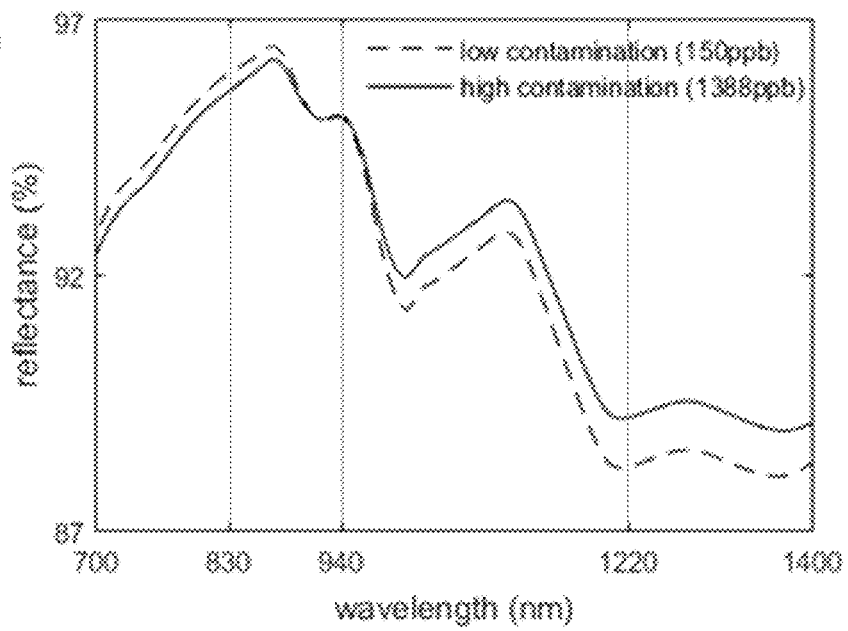

FIG. 3 shows the mean reflection spectra of test maize kernels and the reference DON-contaminated maize powder, measured with the 250 mm-reflection integrating sphere: (a) vis-NIR spectrum; (b) NIR wavelength range showing the largest spectral contrast between the low and high contaminated maize kernels.

Figure 4A:
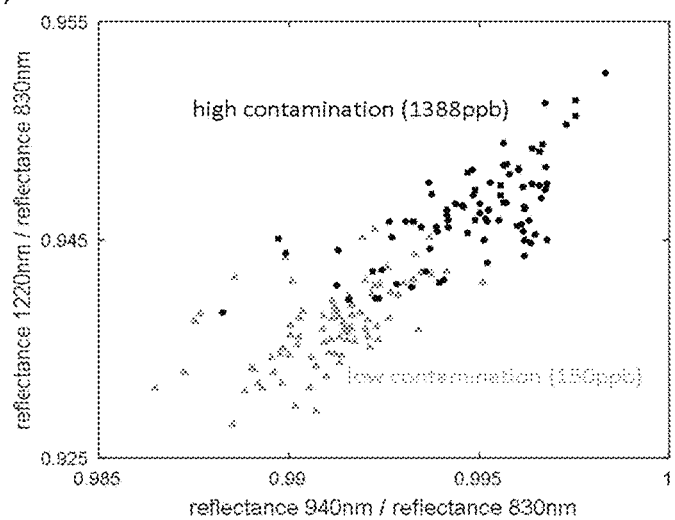
FIGS. 4(a)-4(c) show the spectral difference between test and reference samples, measured with a 250 mm-reflection integrating sphere: (a) contrast between low and high contaminated maize kernels; (b) ratio of reflectances at 940 nm and 830 nm; (c) ratio of reflectances at 1220 nm and 830 nm.
Figure 4C:
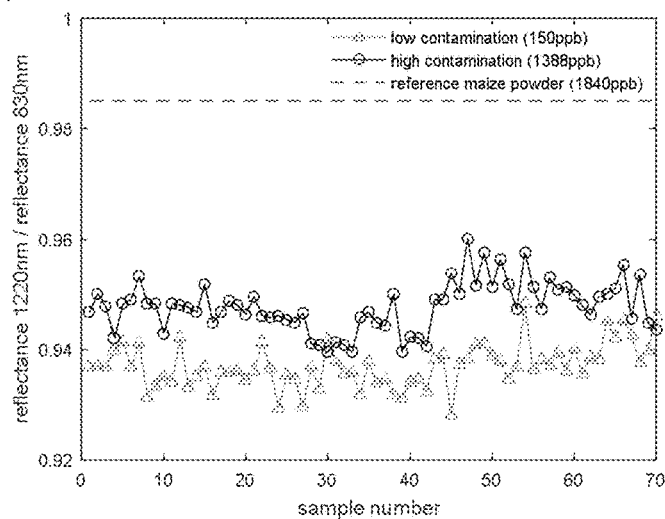

FIG. 4 shows the spectral difference between the test and reference samples, measured with the 250 mm-reflection integrating sphere: (a) contrast between low and high contaminated maize kernels; (b) ratio of reflectances at 940 nm and 830 nm; (c) ratio of reflectances at 1220 nm and 830 nm.

Figure 4B:
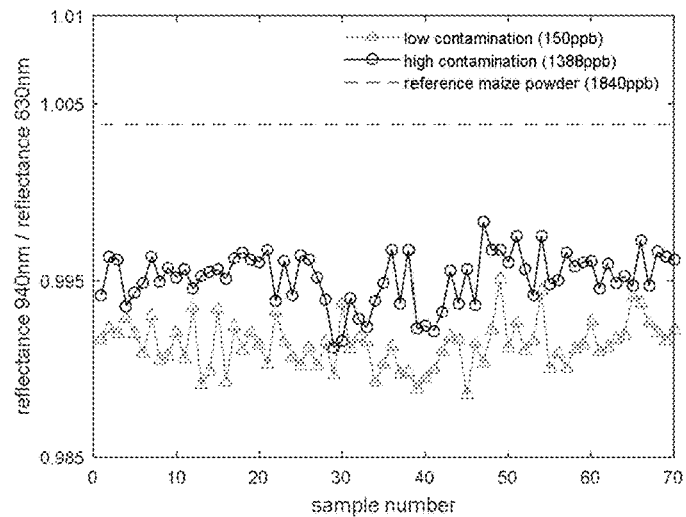

FIG. 4 shows the ratio of the reflectances at 940 nm and 830 nm and the ratio of the reflectances at 1220 nm and 830 nm to visualize the spectral contrast between the low and high contaminated sample. As shown in FIG. 4a, a clear deviation between the low and high contaminated maize sample can be made. Furthermore, when considering the reference DON-contaminated maize powder, much higher reflectance ratios were obtained, namely 1.004±0.002 for the ratio of the reflectances at 940 nm and 830 nm and 0.985±0.004 for the ratio of the reflectances at 1220 nm and 830 nm (FIG. 4a, FIG. 4b). Generally, it can be observed that higher contamination levels give rise to higher reflectance ratios. The low contaminated maize kernels show a larger contrast with the DON-contaminated maize powder than with the high contaminated maize kernels, as a consequence of the higher, homogenous contamination of the maize powder.

Figure 5:
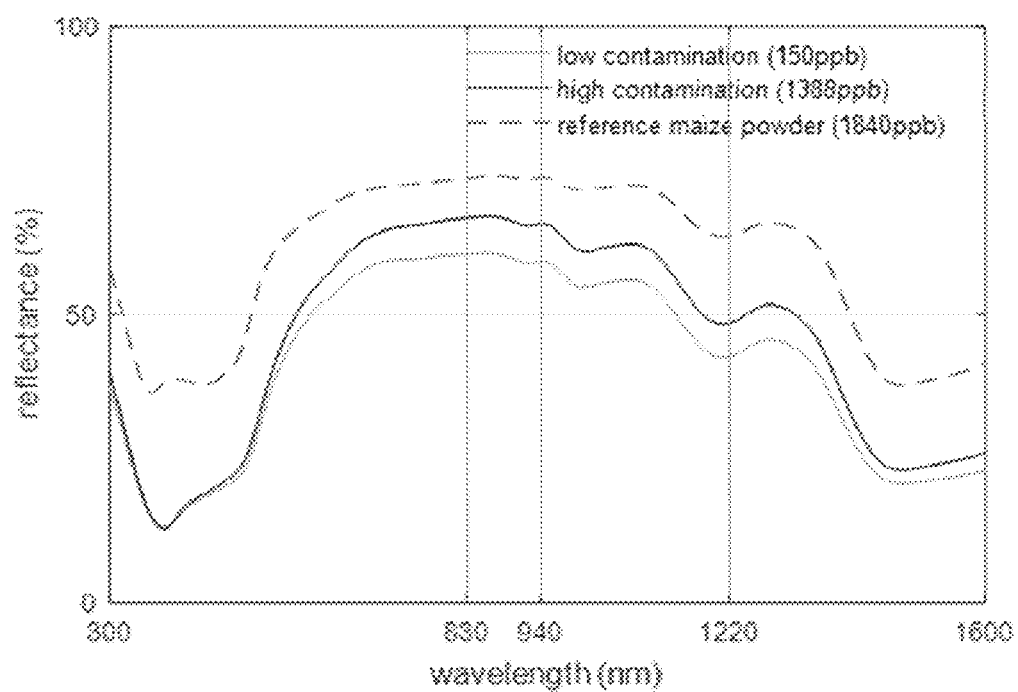
FIG. 5 shows the mean reflection spectrum of test and reference maize samples, measured with a 30 mm-reflection integrating sphere.

In the next step, the reflection spectra of individual low and high contaminated maize kernels, measured with the 30 mm-reflection integrating sphere are investigated. Each sample was illuminated at different positions, allowing to monitor the local contamination differences. Considering the mean reflectance, the tested maize batch and the reference DON-contaminated maize powder show again similar reflectance maxima in the NIR region, as shown in FIG. 5. FIG. 5 shows the mean reflection spectrum of the test and reference maize samples, measured with the 30 mm-reflection integrating sphere. To evaluate the local contamination and the spectroscopic contrast between the samples, the ratios of the reflectances at 830 nm, 940 nm and 1220 nm are calculated.

Figure 6:
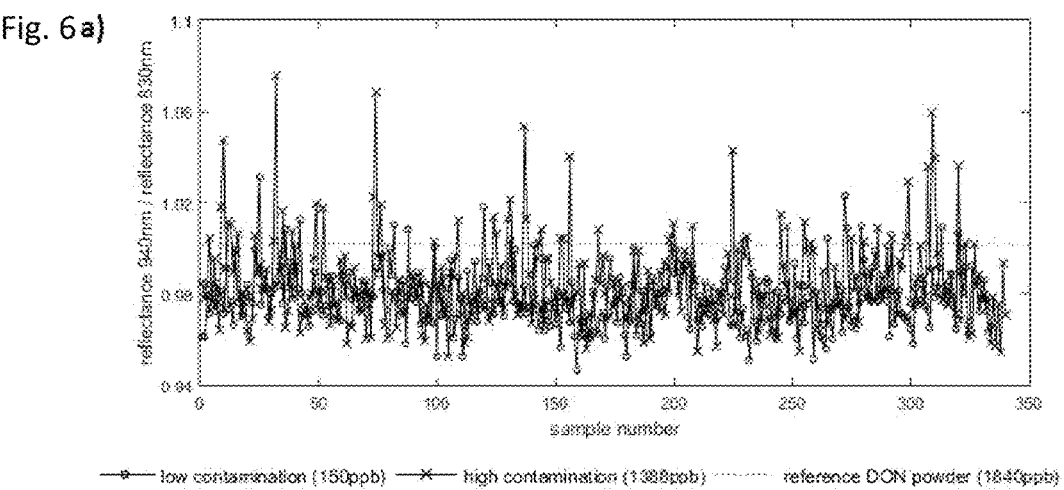
FIGS. 6(a) and 6(b) show a comparison between the reflectance ratios of test and reference samples, measured with a 30 mm-reflection integrating sphere: (a) ratio of the reflectances at 940 nm and 830 nm; (b) ratio of the reflectances at 1220 nm and 830 nm.
Figure 6:
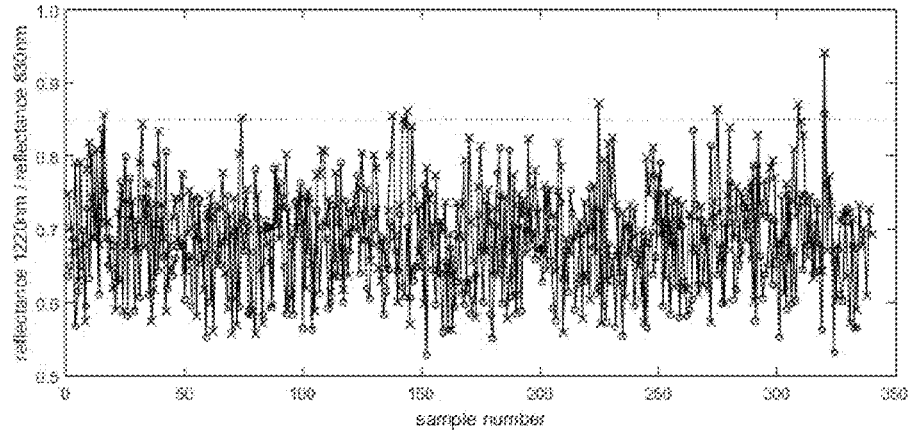

FIG. 6 shows a comparison between the reflectance ratios of the test and reference samples, measured with the 30 mm-reflection integrating sphere: (a) ratio of the reflectances at 940 nm and 830 nm; (b) ratio of the reflectances at 1220 nm and 830 nm.

Considering the reflectance ratios, a contrast between the low and high contaminated samples can be identified in FIG. 6. The high contaminated areas still show the highest reflectance ratios. However, compared to the first-stage measurements, the reflectance ratios show a much larger variation and a less pronounced contrast. This larger variation is caused by the local contamination of the sample. A contaminated maize kernel does mostly not show a homogenous contamination, resulting in different measured ratios for various illumination spots. The mean ratio of the reference DON-contaminated powder, 1.002±0.018 and 0.849±0.062 for the ratio of the reflectances at 940 nm and 830 nm and the ratio of the reflectances at 1220 nm and 830 nm respectively, is situated in-between the reflectance ratios of the contaminated maize kernels. The high contaminated maize kernels, showing a mean contamination level of 1388 ppb, can locally show a higher contamination. A high contaminated maize kernel can, for example, contain a small area with a contamination level larger than 1840 ppb, while the other part of the maize is non-contaminated. Consequently, to avoid the presence of high localized contamination areas, the local contamination level should be investigated, instead of the mean contamination of the maize kernel. When measuring the mean contamination of a collection of maize kernels, the healthy areas on the maize kernel will decrease the mean contamination level, even in the presence of high contaminated maize kernels. To avoid that these high contaminated maize kernels enter the food supply chain, a scanning of the individual maize kernels is indispensable.

To quantitatively compare the performance of both measurement setups and to evaluate the differentiating capability of both reflectance ratios, class difference can be calculated. The class difference (D) is a measure for the difference between the average values (μ) of two product groups, taking the standard deviation (σ) and the amount of measured samples (N) into account (Downie & Health, 1970):

$$D = \frac{|\mu_{contaminated} - \mu_{healthy}|}{\sqrt{\frac{\sigma^2_{contaminated}}{N_{contaminated}} + \frac{\sigma^2_{healthy}}{N_{healthy}}}} \quad (2)$$

The larger the spectral difference between the low and high contaminated maize kernels, the larger the class difference (Table 1). Consequently, the measurements with the 250 mm-reflection integrating sphere show a larger class difference than the measurements with the 30 mm-reflection integrating sphere. However, when considering the mean reflectance ratios, we can observe that the 30 mm-reflection integrating sphere is also able to clearly distinguish between low and high DON-contamination levels. Its lower class difference results from its larger variation, caused by the varying local contamination levels. Comparing the class difference of the two ratios of reflectances, it can be observed that both ratios show a comparable performance. Generally, it can be concluded that the reflectances at 830 nm, 940 nm and 1220 nm enable to differentiate between low and high DON-contaminated maize kernels.

TABLE 1 class difference of the two ratios of reflectances, for both measurement configurations.

| Configuration | Ratio of reflectances | Mean ratio low contamination | Mean ratio high contamination | Class difference |
|---|---|---|---|---|
| 250 mm-reflection integrating sphere | 940 nm/830 nm | 0.991 ± 0.003 | 0.995 ± 0.004 | 15.731 |
| | 1220 nm/830 nm | 0.937 ± 0.010 | 0.948 ± 0.010 | 15.086 |
| 30 mm-reflection integrating sphere | 940 nm/830 nm | 0.979 ± 0.042 | 0.984 ± 0.061 | 4.685 |
| | 1220 nm/830 nm | 0.672 ± 0.165 | 0.704 ± 0.192 | 6.123 |

Figure 7:
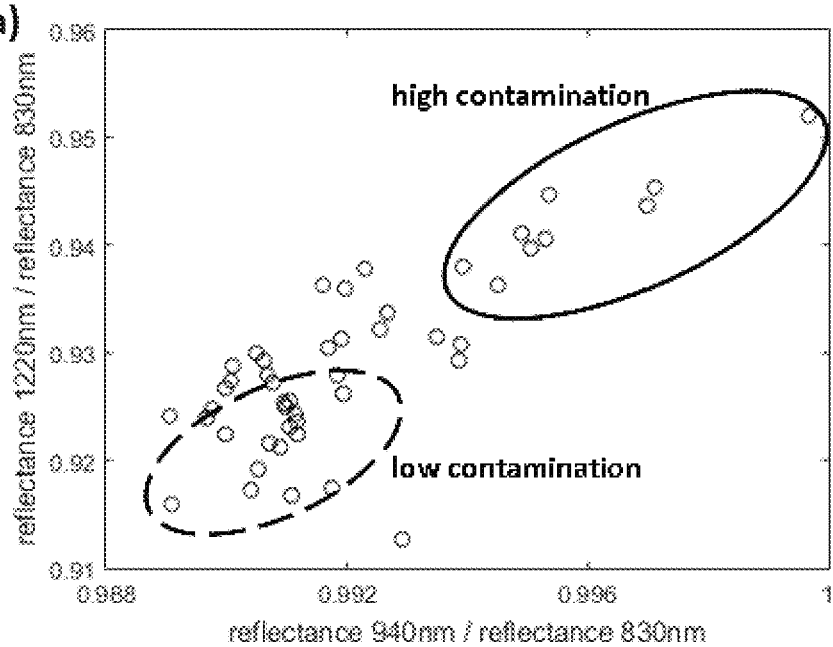
FIGS. 7(a) and 7(b) show classification of a maize batch, based on a 250 mm-reflection integrating sphere configuration: (a) reflectance ratios; (b) mean spectra of the selected Petri dishes.
Figure 7:
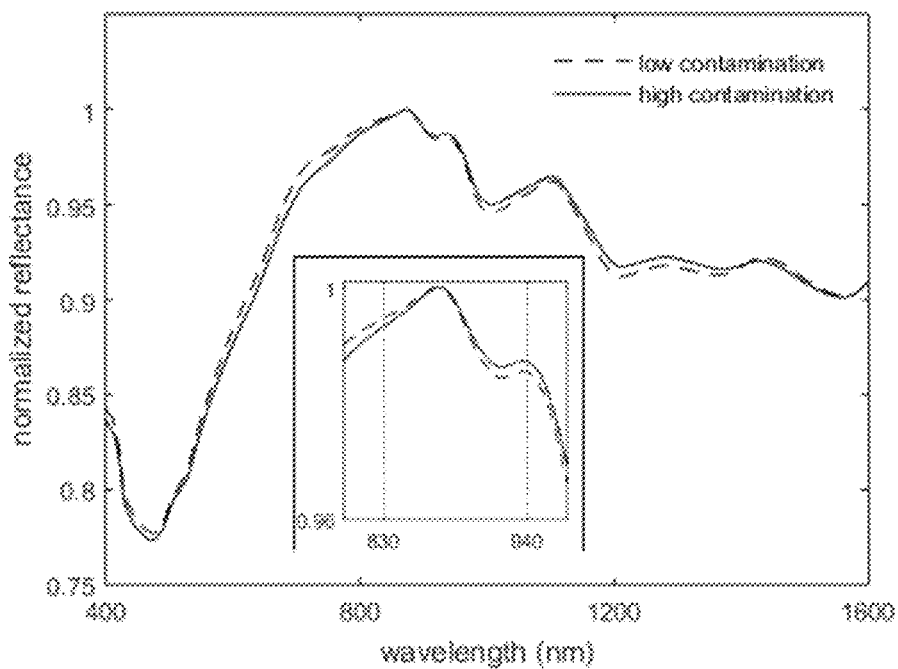

To validate the classification capability of the diffuse reflectance measurement setups described above, the method of the present invention was used to classify a contaminated maize batch into a low and high contaminated subsample. To obtain an efficient classification, we first performed a rough pre-classification with the first stage measurement configuration. Specifically, we measured 50 Petri dishes of maize, each consisting of 15 maize kernels, with the 250mm-reflection integrating sphere and calculated their reflectance ratios. FIG. 7 shows classification of the contaminated maize batch, based on the 250 mm-reflection integrating sphere configuration: (a) reflectance ratios; (b) mean spectra of the selected Petri dishes. The Petri dishes with the highest ratios were classified as high contaminated, the ones with the lowest ratios as low contaminated (indicated by the black and green circle in FIG. 7a). The Petri dishes with intermediate ratios were not considered during this classification process, to maximize the contrast between the obtained low and high contaminated subsamples. Considering the mean spectra of the selected maize Petri dishes, similar spectral differences as for the French low and high contaminated samples can be observed (FIG. 7b).

Figure 8:
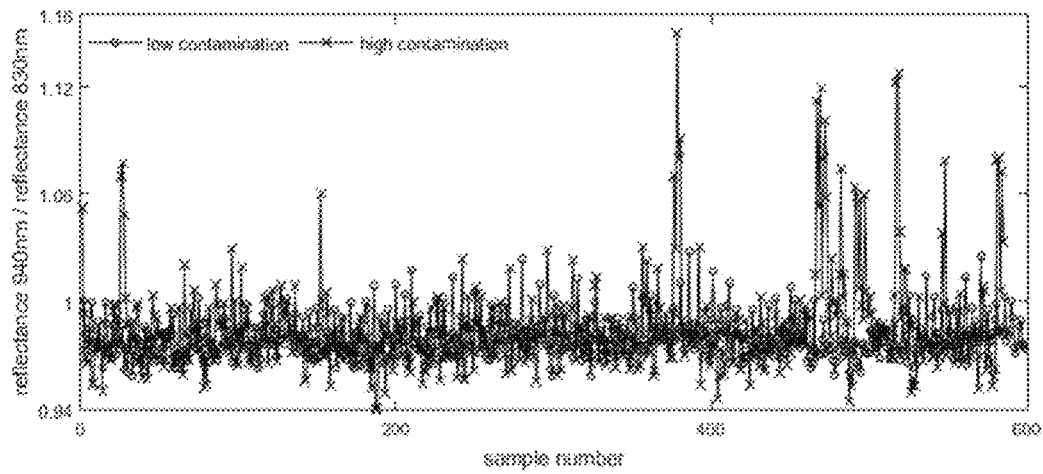
FIGS. 8(a) and 8(b) show a comparison of the reflectance ratios of the low and high contaminated maize samples, measured with a 30 mm-reflection integrating sphere, after pre-classification with the first stage measurement configuration: (a) ratio of the reflectances at 940 nm and 830 nm; (b) ratio of the reflectances at 1220 nm and 830 nm.
Figure 8:
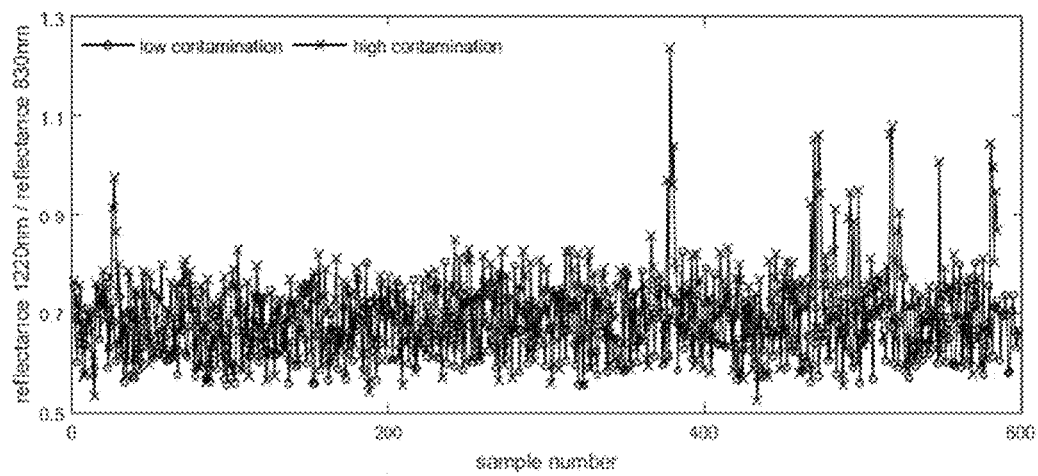

Following, we measured the individual maize kernels of the selected maize Petri dishes using the 30 mm-reflection integrating sphere. Studying the measured reflectance ratios, the highest ratios correspond to the maize kernels of the selected high contaminated Petri dishes. FIG. 8 shows a comparison of the reflectance ratios of the low and high contaminated maize samples, measured with the 30 mm-reflection integrating sphere, after pre-classification with the first stage measurement configuration: (a) ratio of the reflectances at 940 nm and 830 nm; (b) ratio of the reflectances at 1220 nm and 830 nm. Moreover, as with the previous measurements on the test maize batch, the two reflectance ratios show a similar classification performance. However, a large variation on the reflectance ratios of the low and high contaminated maize Petri dishes is observed. When the first stage measurement configuration shows a high reflectance ratio, this indicates the presence of one or more high contaminated maize kernels. Because the 250 mm-reflection integrating sphere measures the mean reflectance of the maize Petri dishes, still different healthy or low contaminated maize kernels can be present in the high contaminated classified Petri dishes. Furthermore, also in the low contaminated Petri dishes, the presence of localized high contaminated areas is still possible, as long as they do not significantly affect the mean optical spectrum. Consequently, this emphasizes the importance of a second classification step, based on the measurements of the local contamination.

To obtain a final low and high contaminated subsample of the contaminated maize batch, we classified the maize kernels of the selected maize Petri dishes on basis of their localized reflectance ratios. Considering the selected high contaminated Petri dishes, the maize kernel was classified as high contaminated when at least one illumination point showed an extremely high reflectance ratio (above 1.03 for the ratio of the reflectances at 940 nm and 830 nm or above 0.80 for the ratio of the reflectances at 1220 nm and 830 nm) or when three or more illumination points showed a high reflectance ratio (above 1.00 for the ratio of the reflectances at 940 nm and 830 nm or above 0.75 for the ratio of the reflectances at 1220 nm and 830 nm). The maize kernels were considered as low contaminated if all five measurement points gave a low reflectance ratio (below 0.99 for the ratio of the reflectances at 940 nm and 830 nm or below 0.70 for the ratio of the reflectances at 1220 nm and 830 nm). After the application of this classification technique, two subsamples of 100 g each were obtained, which were chemically analysed by the CODA-CERVA, the Belgian Reference Laboratory for Mycotoxins. The executed LC-MS/MS analyses indicated a DON-contamination of 18184 ppb for the high contaminated subsample, while a DON-contamination of 654 ppb was obtained for the low contaminated sample. As a result, these contamination levels validate our classification technique, based on the reflectance values at 830 nm, 940 nm and 1220 nm.

The method of the present invention was tested on a low and high naturally contaminated cereal sample, with an a-priori known DON concentration of 150 ppb and 1388 ppb respectively. Studying the reflectance spectra, an optical contrast between 700 nm and 1400 nm could be observed for both measurement stages. Based on the reflectances at 830 nm, 940 nm and 1220 nm, an optical detection criterion could be defined. This detection criterion was first validated by the measurement of a reference DON-contaminated maize powder. Secondly, it was used to successfully split a contaminated batch, with a-priori unknown DON-concentration, in a low and high contaminated subsample, of which subsequent chemical analyses indicated a DON-concentration of 645 ppb and 18184 ppb respectively. Because the detection criterion uses commercial available laser lines, this result paves the way to an ultra-fast, laser-based optical detection, usable immediately after the harvest, without pre-processing or grinding of the cereal.

The above measurement results clearly indicate the use of diffuse reflectance spectroscopy as a promising detection technique for the identification of DON in maize kernels. Moreover, the commercial availability of the NIR laser lines, optical filters and sensitive detectors allow its integration in practical systems. In contrast to the current sample-based chemical analyses, the optical classification technique of the present invention provides an ultra-fast and non-destructive alternative, which does not require any pre-processing or grinding of the cereal.

Because the mean contamination level of a collection of maize kernels often gives a wrong interpretation of the localized contamination levels, a localized screening of individual maize kernels is beneficial.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A method for detecting the presence of mycotoxins in cereals, the method comprising:
   capturing at least one diffuse-light absorption spectrum of a collection of cereal grains;
   capturing at least one diffuse-light absorption spectrum of an individual cereal grain from the collection of cereal grains; and
   classifying the level of mycotoxin contamination in at least one cereal grain by performing multivariate data analysis on the at least one diffuse-light absorption spectrum of the collection of cereal grains and the at least one diffuse-light absorption spectrum of the individual cereal grain.

2. The method of claim 1 wherein each diffuse-light absorption spectrum is captured using an integrating sphere.

3. The method of claim 1 wherein the step of capturing at least one diffuse-light absorption spectrum of an individual cereal grain comprises capturing multiple diffuse-light absorption spectra by illuminating multiple regions of the cereal grain.

4. The method of claim 1 wherein the step of classifying the level of mycotoxin contamination in at least one cereal grain comprises calculating the ratio between the reflectance at a first selected wavelength and the reflectance at a second selected wavelength; and classifying the level of mycotoxin contamination in at least one cereal grain based on the calculated ratio.

5. The method of claim 4 wherein the selected wavelengths are in the wavelength region of 700 nm to 1500 nm.

6. The method of claim 1 wherein the step of classifying the level of mycotoxin contamination in at least one cereal grain uses chemometric techniques.

7. The method of claim 1 wherein the step of classifying the level of mycotoxin contamination in at least one cereal grain comprising comparing at least one captured spectrum with a spectrum of an uncontaminated grain and identifying differences between the spectra.

8. The method of claim 7 further comprising obtaining the spectrum of an uncontaminated grain from a database of grain spectra.

9. The method of claim 8 further comprising identifying the cereal type of the collection of cereal grains by comparing at least one captured spectrum to a plurality of sample spectra in the database to find the best fit.

10. The method of claim 1 further comprising calculating a mean diffuse-light absorption spectrum of a collection of cereal grains if multiple diffuse-light absorption spectra are captured and wherein the step of classifying the level of mycotoxin contamination in at least one cereal grain comprises performing multivariate data analysis on a mean spectrum.

11. The method of claim 1 further comprising calculating a mean diffuse-light absorption spectrum of at least one cereal grain if multiple diffuse-light absorption spectra of the cereal grain are captured and wherein the step of classifying the level of mycotoxin contamination in at least one cereal grain comprises performing multivariate data analysis on a mean spectrum.

12. An apparatus for detecting the presence of mycotoxins in cereals, comprising:
   means for capturing at least one diffuse-light absorption spectrum of a collection of cereal grains;
   means for capturing at least one diffuse-light absorption spectrum of an individual cereal grain from the collection of cereal grains; and
   means for classifying the level of mycotoxin contamination in at least one cereal grain by performing multivariate data analysis on the at least one diffuse-light absorption spectrum of the collection of cereal grains and the at least one diffuse-light absorption spectrum of the individual cereal grain.

13. The apparatus of claim 12 wherein each means for capturing a diffuse-light absorption spectrum comprises an integrating sphere.

14. The apparatus of claim 12 wherein the means for capturing at least one diffuse-light absorption spectrum of the individual cereal grain comprises an integrating sphere which is smaller than that used to capture each diffuse-light absorption spectrum of the collection of cereal grains.

15. A computer readable medium containing program instructions which when executed by a processor cause the processor to perform the method of claim 1.

* * * * *